United States Patent [19]
Takano et al.

[11] Patent Number: 5,916,782
[45] Date of Patent: Jun. 29, 1999

[54] PROCESS FOR PRODUCING ASPARTASE AND PROCESS FOR PRODUCING L-ASPARTIC ACID

[75] Inventors: Junichi Takano; Kuniki Kino, both of Hofu, Japan

[73] Assignee: Kyowa Hakko Kogyo Co., Ltd., Tokyo, Japan

[21] Appl. No.: 08/822,002

[22] Filed: Mar. 24, 1997

[30] Foreign Application Priority Data

Mar. 29, 1996 [JP] Japan ................................. 8-075989

[51] Int. Cl.$^6$ ............................ C12P 13/20; C12P 21/00; C12N 9/88
[52] U.S. Cl. ...................... 435/109; 435/232; 435/71.1; 435/71.2
[58] Field of Search ...................... 435/109, 232, 435/71.1–71.2

[56] References Cited

U.S. PATENT DOCUMENTS

| 4,436,813 | 3/1984 | Wood et al. ............................ 435/109 |
| 4,560,653 | 12/1985 | Sherwin et al. ........................ 435/109 |
| 4,698,224 | 10/1987 | Nakanishi et al. ........................ 426/4 |
| 5,441,634 | 8/1995 | Edwards et al. ........................ 210/194 |
| 5,541,090 | 7/1996 | Sakano et al. ........................... 435/109 |

FOREIGN PATENT DOCUMENTS

| 102207 | 3/1984 | European Pat. Off. . |
| 0 110 422 | 6/1984 | European Pat. Off. . |
| 102207 | 7/1984 | European Pat. Off. . |
| 0 127 940 | 12/1984 | European Pat. Off. . |
| 0 683 231 | 11/1995 | European Pat. Off. . |
| 0 736 603 | 10/1996 | European Pat. Off. . |
| 0 823 482 | 2/1998 | European Pat. Off. . |
| 54-12553 | 5/1979 | Japan . |
| 57-18867 | 4/1982 | Japan . |
| 60-133883 | 7/1985 | Japan . |
| 3-55103 | 8/1991 | Japan . |
| 5-30977 | 2/1993 | Japan . |
| 2 108 128 | 5/1983 | United Kingdom . |

OTHER PUBLICATIONS

"Reaction Process. A New Production Process of L–Aspartic Acid" Masato, et al. (1994) vol. 58 No. 11 pp. 878–882, (with English abstract).

Smith et al. (1984) Eur. Congr. Biotechnol. 3 Meet, 1, "Biosynthesis of Aspartase and Production of Aspartic Acid ina Hollow Membrane Fiber Immobilized–Cell Reactor", p. 475, in Biotechds, AN 85–11128.

*Primary Examiner*—Jon P. Weber
*Attorney, Agent, or Firm*—Antonelli, Terry, Stout & Kraus, LLP

[57] ABSTRACT

Disclosed are a process for producing aspartase which comprises culturing a microorganism belonging to the genus Escherichia being capable of producing aspartase in a medium until aspartase is produced and accumulated in the culture, and recovering aspartase therefrom, wherein dissolved oxygen concentration of the medium is in the range of 0 to 1 ppm on the stage that microbial growth is middle and/or late logarithmic growth phase; and a process for producing L-aspartic acid which comprises converting fumaric acid and ammonia into L-aspartic acid in an aqueous medium in the presence of an enzyme source, wherein said enzyme source is a culture produced in accordance with said aspartase-producing process, cells isolated from the culture, or processed cells thereof.

4 Claims, No Drawings

PROCESS FOR PRODUCING ASPARTASE AND PROCESS FOR PRODUCING L-ASPARTIC ACID

FIELD OF THE INVENTION

The present invention relates to a process for producing aspartase using a microorganism belonging to the genus Escherichia having the ability to produce and accumulate said aspartase, and to a process for producing L-aspartic acid using said aspartase.

BACKGROUND OF THE INVENTION

There have heretofore been known many reports referring to processes for producing L-aspartic acid from fumaric acid and ammonia using aspartase as produced by microorganisms (Japanese Published Examined Patent Application Nos. 54-12553 and 57-18867). As such microorganisms, known are those belonging to the genera Escherichia and Corynebacterium, and some attempts have heretofore been made to obtain mutants with high aspartase productivity through genetic recombination technology (Japanese Published Unexamined Patent Application Nos. 60-133883 and 5-30977).

In the process for producing aspartase in a large amount using such microorganisms of the genera Escherichia and Corynebacterium, fumaric acid, which is expensive, is used as the nutrient source. In the process for producing aspartase using a transformant with high aspartase productivity as obtained through genetic recombination, antibiotics are added to the seed media for ensuring the stability of aspartase productivity of the transformant.

It is known that, when a microorganism of the type capable of producing and accumulating aspartame along with fumarase is used to produce aspartase and said aspartase is used for producing L-aspartic acid, some by-products other than L-aspartic acid are produced due to said fumarase to thereby lower the yield of the intended L-aspartic acid. In order to prevent the reduction in the yield of L-aspartic acid, the system is heat-treated or treated with acids after the production of aspartase to thereby remove fumarase activity from the system (Kagaku Kogyo, 58, 878, 1994; Japanese Published Examined Patent Publication No. 3-55103).

The prior art techniques are problematic in that processes, using microorganisms being capable of producing aspartase in order to produce-large amounts of aspartase, require fumaric acid, which is expensive, as the nutrient source; processes using transformants with high aspartase productivity as obtained through genetic recombination require antibiotics to be added to the seed media for ensuring the stability of aspartase productivity of the trasansformant; and in the processes for producing L-aspartic acid using microorganisms that may produce and accumulate fumarases in addition to the intended aspartase, the production of by-products other than the intended L-aspartic acid is inevitable.

SUMMARY OF THE INVENTION

According to the present invention, provided is a process for producing aspartase which comprises culturing a microorganism belonging to the genus Escherichia being capable of producing aspartase in a medium until aspartase is produced and accumulated in the culture, and recovering aspartase therefrom, wherein dissolved oxygen concentration of the medium is in the range of 0 to 1 ppm on the stage that microbial growth is middle and/on late logarithmic growth phase; and a process for producing L-aspartic acid which comprises converting fumaric acid and ammonia into L-aspartic acid in an aqueous medium in the presence of an enzyme source, wherein said enzyme source is a culture produced in accordance with said aspartase-producing process, cells isolated from the culture, or processed cells thereof.

DETAILED DESCRIPTION OF THE INVENTION

In the present invention, any microorganism can be used so long as it belongs to the genus Escherichia, preferably *Escherichia coli*, and is capable of producing aspartame, preferably producing a large amount of aspartame, can be used.

In general, *Escherichia coli* may have the ability to produce and accumulate aspartase. As an example, mentioned is *Escherichia coli* ATCC-11303.

The suitable microorganism used in the present invention can be obtained as a mutant strain producing a large amount of aspartase by subjecting aspartase-producing microorganisms belonging to the genus Escherichia to the conventional mutagenesis, screening the resulting mutants to select those capable of more rapidly growing in minimal media containing L-aspartic acid as the sole nitrogen source (Appl. Env. Microbiol., 48, 1072, 1984). Such mutant strains include *Escherichia coli* EAPc7, *Escherichia coli* EAPc244, *Escherichia coli* EAPc28, *Escherichia coli* EAPc110, *Escherichia coli* EAPc130 (Japanese Published Unexamined Application No. 60-133883), and *Escherichia coli* H-9183.

The suitable microorganism used in the present invention can be obtained as a transformant producing a large amount of aspartame by use of genetic recombination technology. Such transformants include *Escherichia coli* TA5003, *Escherichia coli* TA5004, and *Escherichia coli* TA5005 (Japanese Published Unexamined Patent Application No. 60-133883).

It is possible to produce aspartase by culturing a microorganism of the present invention according to the process mentioned below.

As the medium, any of a natural medium and a synthetic medium may be used so long as it contains carbon sources, nitrogen sources, inorganic substances and other nutrients required for the microorganism used, etc., which can be assimilated by the microorganism used and the microorganism can be efficiently cultured therein.

As the carbon source, carbohydrate such as glucose, fructose, sucrose, molasses containing these, and even starch and starch hydrolysates; organic acid such as acetic acid, fumaric acid, lactic acid and propionic acid; and alcohol such as ethanol, glycerin and propanol, etc. can be used.

As the nitrogen source, ammonia, various inorganic or organic ammonium salt such as ammonium chloride, ammonium sulfate, ammonium acetate and ammonium phosphate; amines; other nitrogen-containing compounds; peptone, meat extract, yeast extract, corn steep liquor, casein hydrolysate, bean cake, bean cake hydrolysate, various cultured cells and cell digested product, etc. can be used.

As the inorganic substance, potassium dihydrogenphosphate, dipotassium hydrogenphosphate, magnesium phosphate, magnesium sulfate, sodium chloride, ferrous sulfate, manganese sulfate, copper sulfate, and calcium carbonate, etc. can be used.

Aerating conditions or stirring conditions during culturing have great influences on the level of accumulation of aspartase.

The microorganism of the present invention is cultured under aerobic condition until early logarithmic growth phase, after then it is cultured in a controlled aeration condition in which the dissolved oxygen concentration in the medium is in the range of 0 to 1 ppm, whereby the production and accumulation of fumarase is reduced and the production and accumulation of the intended aspartase is increased.

Culturing is carried out at a temperature of 20 to 40° C., preferably 25 to 37° C. The pH of the medium is in the range of 5 to 9, preferably 6 to 8. The pH is adjusted with calcium carbonate, inorganic or organic acid, alkaline solution, ammonia, a pH buffer agent or the like. Generally, after culturing for 3 to 24 hours, a large amount of aspartase is accumulated in the cells of the microorganism.

After the completion of the culturing, aspartase is isolated and purified from the culture by a conventional method. For example, the culture is centrifuged to collect the cells, and the cells are washed and disrupted with an ultrasonic disrupter, a French press, a Manton-Gaulin homogenizer, a Dyno mill or the like to obtain a cell-free extract. The cell-free extract is centrifuged, and the resulting supernatant is subjected to salting out with ammonium sulfate or the like, to anion-exchange chromatography with diethylaminoethyl (DEAE)-Sepharose or the like, to hydrophobic chromatography with butyl-Sepharose, phenyl-Sepharose or the like, to gel permeation with a molecular sieve or the like, or to electrophoresis such as isoelectric electrophoresis, thereby obtaining a pure product of aspartase.

The enzyme activity of aspartase can be determined in the manner mentioned below.

A sample is incubated in an aqueous solution comprising ammonium fumarate (160 g/liter, pH 8.7) and $MgCl_2$ (0.2 mM) at 37° C. for 60 minutes. The resulting L-aspartic acid is determined using high-performance liquid chromatography. The enzyme activity of aspartase is represented in units, with a unit (U) being defined as the activity capable of producing of 1 μmol of L-aspartic acid in one minute is referred to as one unit (U).

Fumarase activity may be determined in the manner mentioned below.

A sample is incubated in an aqueous solution comprising sodium fumarate (1 M, pH 8.0) at 37° C. for 30 minutes. The resulting malic acid is determined using high-performance liquid chromatography. The activity of the sample that produces 1 μmol of malic acid in one minute is referred to as one unit (U).

L-aspartic acid can be produced using, as an enzyme source, a culture containing aspartase in a large amount obtained in the above process for producing aspartase, cells isolated from the culture, or processed cells thereof, by adding fumaric acid and ammonia to an aqueous medium suitable for enzyme reaction to produce and accumulate L-aspartic acid therein, and by recovering the accumulated L-aspartic acid therefrom.

The processed cells includes dried cells, freeze-dried cells, surfactant-treated cells, enzymatically treated cells, ultrasonically treated cells, mechanically ground cells, solvent-treated cells, protein containing fractions of the cells and immobilized products of cells or processed cells.

Enzyme which is obtained by extraction from the cells and has enzyme activity of aspartase, purified preparation thereof, and immobilized products thereof are also used as the processed cells.

The aqueous medium includes water, buffer such as phosphate buffer, carbonate buffer, acetate buffer, borate buffer, citrate buffer and tris buffer, alcohol such as methanol and ethanol, ester such as ethyl acetate, ketone such as acetone, and amide such as acetamide.

The culture obtained in the above process for producing aspartase is also employed as the aqueous medium, either directly or after having been diluted 1- to 10-fold, preferably 2- to 6-fold.

The activity of the enzyme source in the reaction system may be determined, for example, depending on the amount of the substrate used. In general, the enzyme activity in the aqueous medium may be in the range of 10 to 1000 U/liter, preferably 50 to 300 U/liter.

The amount of fumaric acid in the aqueous medium may be usually in the range of 50 to 200 g/liter.

The reaction of fumaric acid with ammonia in an aqueous medium in the presence of an enzyme source is usually conducted at 10 to 50° C. and at a pH of 7.5 to 9.5 for 0.5 to 20 hours.

After the completion of the reaction, an acid such as sulfuric acid and hydrochloric acid is added to the reaction mixture to adjust the pH at 2.7, whereby L-aspartic acid formed is crystallized, and the crystallized L-aspartic acid is collected from the reaction mixture.

The present invention is described in more detail with reference to the following examples, which, however, are not intended to restrict the scope of the invention.

EXAMPLE

Example 1

Production of Aspartase

*Escherichia coli* ATCC-11303 (a wild type strain) being capable of producing aspartame, and *Escherichia coli* H-9183 derived from *E. coli* ATCC-11303 and being capable of producing a large amount of aspartase were used. H-9183 strain was derived from ATCC-11303 strain according to the process mentioned below.

ATCC-11303 strain was subjected to mutagenesis in an aqueous solution containing N-methyl-N'-nitro-N-nitrosoguanidine (0.25 mg/ml) at 30° C. for 30 minutes. About 80,000 strains were obtained through the mutagenesis and screened on the basis of their growing rates in a minimal medium containing L-aspartic acid as the sole nitrogen source. Among the strains thus selected, H-9183 strain which has high growing rate is obtained as a strain capable of producing a large amount of aspartase.

Each of ATCC-11303 and H-9183 strains was cultured with shaking aerobically at 30° C. for 12 hours in a seed medium containing 2% glucose, 2% peptone, 0.3% meat broth, and 0.5% calcium carbonate. The resulting seed culture (10 ml) was inoculated into 1 liter of a medium containing 2% glucose, 0.5% corn steep liquor, 0.03% ammonium sulfate and 0.3% potassium dihydrogen phosphate in a 2L-jar fermentor and culturing was carried out at 30° C. with stirring at 800 rpm. During the culturing, the pH of the medium was kept at about 6.5±0.2 with aqueous ammonia, and the culturing was carried out until glucose in the medium was completely consumed. The culturing was carried out in two ways; one being to culture the microorganism aerobically by aerating the medium at an aeration rate of 1 liter/min throughout the culturing period, and the other being to culture the microorganism with converting the aerobic condition at an aeration rate of 1 liter/min into a controlled aeration condition in the course of the culturing period. The timing of converting the aerobic condition into a controlled aeration condition was on the stage that microbial growth is middle logarithmic growth phase. The amount of aeration into the medium was lowered to make dissolved oxygen concentration of the medium in the range of 0 to 1 ppm as for the controlled aeration condition.

After the completion of the culturing, the aspartase activity and the fumarase activity of the cells of the microorganism were determined.

The results are shown in Table 1.

TABLE 1

| Strain | Culturing Method | Aspartase Activity (U/mg-protein) | Fumarase Activity (U/mg-protein) |
|---|---|---|---|
| ATCC-11303 | Aerobic | 1.0 | 1.2 |
| ATCC-11303 | Aerobic → Controlled aeration | 2.0 | 0.4 |
| H-9183 | Aerobic | 91 | 1.6 |
| H-9183 | Aerobic → Controlled aeration | 117 | 0.7 |

Both ATCC-11303 strain and H-9183 strain that had been cultured under the controlled aeration condition had increased aspartase activities and lowered fumarase activities, respectively.

Example 2

Production of L-aspartic acid

The cultures of H-9183 strain as obtained in Example 1 were suitably diluted, to which was added fumaric acid to the concentration of 100 g/liter. Then, ammonia was added thereto to adjust the pH at 8.7. The reaction was carried out at 30° C. with gently stirring.

The results are shown in Table 2.

TABLE 2

| Culturing Method | Dilution Rate | Time (hr) | L-aspartic Acid (g/liter) |
|---|---|---|---|
| Aerobic | ×½ | 7.5 | 111 |
| Aerobic | ×⅙ | 10.5 | 105 |
| Aerobic → Controlled aeration | ×⅙ | 7.5 | 113 |

The results show that the productivity of L-aspartic acid and the conversion into the product were increased in the culture as obtained at the condition through aeration followed by controlled aeration.

Example 3

Production of L-aspartic acid

The culture of H-9183 strain as obtained in the controlled aeration condition in Example 1 was centrifuged to isolate the cells. The cells were suspended in a phosphate buffer (0.01 M potassium phosphate; pH 7.4), and homogenized along with glass beads to disrupt them into an extract. The extract was passed through a column filled with a resin, Duolite A-7 to thereby make the protein existing in the extract adsorbed by the resin. Then, an aqueous solution of fumaric acid (150 g/liter; adjusted the pH at 8.5 with aqueous ammonia) was passed through the column at 37° C. to thereby obtain a solution of L-aspartic acid (171 g/liter). The pH of the solution(1 liter) was adjusted to 2.7 with sulfuric acid, and 161 g of L-aspartic acid crystals was obtained.

INDUSTRIAL APPLICABILITY

According to the process of the present invention for producing aspartase, it is possible to produce a large amount of aspartase with decreasing a ratio of fumarase/aspartase. In addition, using the aspartase thus produced according to the invention, it is possible to produce pure L-aspartic acid containing less amount of by-products.

What is claimed is:

1. A process for producing aspartase, which comprises culturing a microorganism belonging to the genus Escherichia, being capable of producing aspartase, in a medium until aspartase is produced and accumulated in a culture, and recovering aspartase therefrom; wherein said microorganism is cultured while aerating or stirring said culture under aerobic conditions wherein a dissolved oxygen concentration of the medium is more than 1 ppm during early logarithmic growth phase, and in a controlled aeration condition in which the dissolved oxygen concentration of the medium is in a range of 0 to 1 ppm during middle and/or late logarithmic growth phase.

2. A process for producing aspartase according to claim 1, wherein said culturing is carried out at a temperature in a range of 20° to 40° C., with said medium being at a pH in a range of 5 to 9.

3. A process for producing aspartase according to claim 3, wherein said microorganism is an *Escherichia coli*.

4. A process for producing L-aspartic acid, which comprises converting fumaric acid and ammonia into L-aspartic acid in an aqueous medium, in the presence of (1) a culture produced by a process which comprises culturing a microorganism belonging to the genus Escherichia and capable of producing aspartase in a medium, (2) cells isolated from the culture, or (3) processed cells prepared from the cells isolated from the culture selected from the group consisting of dried cells and freeze-dried cells; wherein said microorganism is cultured while aerating or stirring said culture under aerobic conditions in which a dissolved oxygen concentration of the medium is more than 1 ppm during early logarithmic growth phase, and in a controlled aeration condition in which the dissolved oxygen concentration of the medium is in a range of 0 to 1 ppm during middle and/or late logarithmic growth phase.

* * * * *